United States Patent [19]

Rose

[11] Patent Number: 5,516,773
[45] Date of Patent: May 14, 1996

[54] AGENT FOR TREATING HIGH BLOOD PRESSURE AND CARDIAC INSUFFICIENCY

[75] Inventor: Peter Rose, Biberach, Germany

[73] Assignee: Dr. Karl Thomae GmbH, Biberach an der Riss, Germany

[21] Appl. No.: 104,224

[22] Filed: Aug. 9, 1993

Related U.S. Application Data

[63] Continuation of Ser. No. 832,244, Feb. 7, 1992, abandoned, which is a continuation of Ser. No. 509,129, Apr. 16, 1990, abandoned, which is a division of Ser. No. 265,388, Oct. 31, 1988, abandoned.

[30] Foreign Application Priority Data

Oct. 30, 1987 [DE] Germany .................. 37 36 866.4

[51] Int. Cl.$^6$ ................................. A61K 31/55
[52] U.S. Cl. ................................. 514/213
[58] Field of Search ........................ 514/213

[56] References Cited

FOREIGN PATENT DOCUMENTS 1548844  7/1979  United Kingdom .

OTHER PUBLICATIONS

Roberger et al. European Heart Journal (1987) 8 (Supplementl) 53–59.

*Primary Examiner*—Zohreh Fay
*Attorney, Agent, or Firm*—A. R. Stempel; M-E. M. Devlin

[57] ABSTRACT

The use of a compound of formula

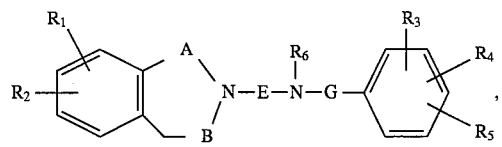

wherein the substituents are defined herein and the physiologically acceptable acid addition salts thereof for treating high blood pressure and cardiac insufficiency.

3 Claims, 3 Drawing Sheets

AGENT FOR TREATING HIGH BLOOD PRESSURE AND CARDIAC INSUFFICIENCY

This is a continuation, of application Ser. No. 07/832,244, filed Feb. 7, 1992, now abandoned which is a continuation of application Ser. No. 509,129, filed Apr. 16, 1990, now abandoned which is a divisional of application Ser. No. 265,388, filed Oct. 31, 1988, (abandoned).

EP-B-0.065.229 describes the compound of formula

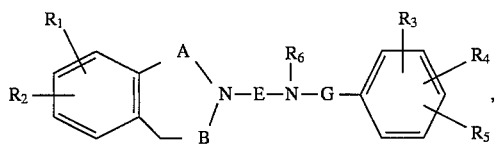

wherein

A represents a —$CH_2$—$CH_2$—, —CH=CH—,

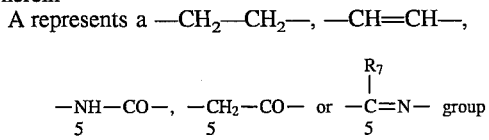

wherein $R_7$ represents an alkyl group having 1 to 3 carbon atoms, and B represents a methylene or carbonyl group or A represents a —CO—CO— group and B represents a methylene group, E represents an ethylene, n-propylene or n-butylene group optionally substituted by an alkyl group with 1 to 3 carbon atoms, an n-propylene group substituted by a hydroxy group in the 2 position or an n-butylene group substituted by a hydroxy group in the 2 or 3 position, G represents a methylene or ethylene group optionally substituted by an alkyl group with 1 to 3 carbon atoms, $R_1$ and $R_2$, which may be identical or different, represent hydroxy groups, alkyl, alkoxy or phenylalkoxy groups in which the alkyl moiety may contain from 1 to 3 carbon atoms, or one of the groups $R_1$ or $R_2$ may also represent a hydrogen atom or $R_1$ together with $R_2$ represents an alkylenedioxy group with 1 or 2 carbon atoms, $R_3$ and $R_4$, which may be identical or different, represent hydrogen or halogen atoms, hydroxy groups, alkyl or alkoxy groups each having 1 to 4 carbon atoms, trifluoromethyl or cyano groups or one of the groups $R_3$ or $R_4$ may also represent a nitro group or $R_3$ together with $R_4$ represents an alkylenedioxy group with 1 or 2 carbon atoms, $R_5$ represents a hydrogen atom, an alkyl, hydroxy, alkoxy, amino, alkylamino, dialkylamino, alkanoylamino, alkoxycarbonylamino or bis(alkoxycarbonyl)amino group wherein the alkyl part may contain from 1 to 3 carbon atoms, or a methylamino or ethylamino group substituted by a trifluoromethyl group, and $R_6$ represents a hydrogen atom, an alkyl, phenylalkyl, alkanoyl or alkoxycarbonyl group in which the alkyl moiety may contain from 1 to 3 carbon atoms, or an alkylene group with 3 to 5 carbon atoms.

and the acid addition salts thereof, particularly the physiologically acceptable acid addition salts thereof with inorganic or organic acids, and the specification points out that this compound and the acid addition salts thereof have valuable pharmacological properties, e.g. a long-lasting heart rate lowering effect and the effect of reducing the $O_2$ requirement of the heart.

The compounds have therefore been developed as novel substances which lower heart rate by acting directly on the sinoatrial node. As a result, the substances have anti-ischaemic properties, i.e. in addition to lowering the myocardial energy consumption by the heart rate they simultaneously increase the oxygen supply by extending the diastole. Pharmacological investigations have shown that the substances do not affect either inotropy or blood pressure or the AV transmission. Experiments on animals have shown an additional so-called myocardioprotective effect. Thus, the substances appear to be suitable for the treatment of stable coronary heart disease.

Tests on humans have surprisingly shown that the substances have valuable hypotensive properties.

The invention therefore relates to the use of the compounds of general formula I and the acid addition salts thereof, particularly the physiologically acceptable acid addition salts thereof with inorganic or organic acids, for treating high blood pressure and/or cardiac insufficiency.

The invention further relates to the use of these compounds and the acid addition salts thereof for the manufacture of a pharmaceutical preparation for the treatment of high blood pressure and/or cardiac insufficiency.

Preferably, 1,3,4,5-tetrahydro-7,8-dimethoxy- 3-[3-[[2-(3,4-dimethoxyphenyl)ethyl]methyl]amino]propyl]-2H-3-benzazepin-2-one and the physiologically acceptable acid addition salts thereof are used, especially the hydrochloride, which is hereinafter referred to as UL-FS 49 CL.

The daily dose is expected to be 0.015 to 0.2 mg/kg of body weight, preferably 0.0175 mg/kg to 0.175 mg/kg of body weight, twice a day, for example the expected therapeutic dosage for lowering arterial blood pressure will probably be between 1.25 and 7.5 mg per person by oral route twice a day. The exact dose will obviously depend on the patient's condition and the corresponding prognosis of the disease and might deviate from the dosage specified above.

For medicinal use, the drug may be formulated with conventional galenic excipients such as lactose, mannitol, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, carboxymethylcellulose or fatty substances such as hard fat or suitable mixtures thereof to produce conventional preparations such as plain or coated tablets, capsules, powders, suspensions, drops, ampoules, syrups or suppositories.

The effect of the compounds was determined as follows.

Figure 1:
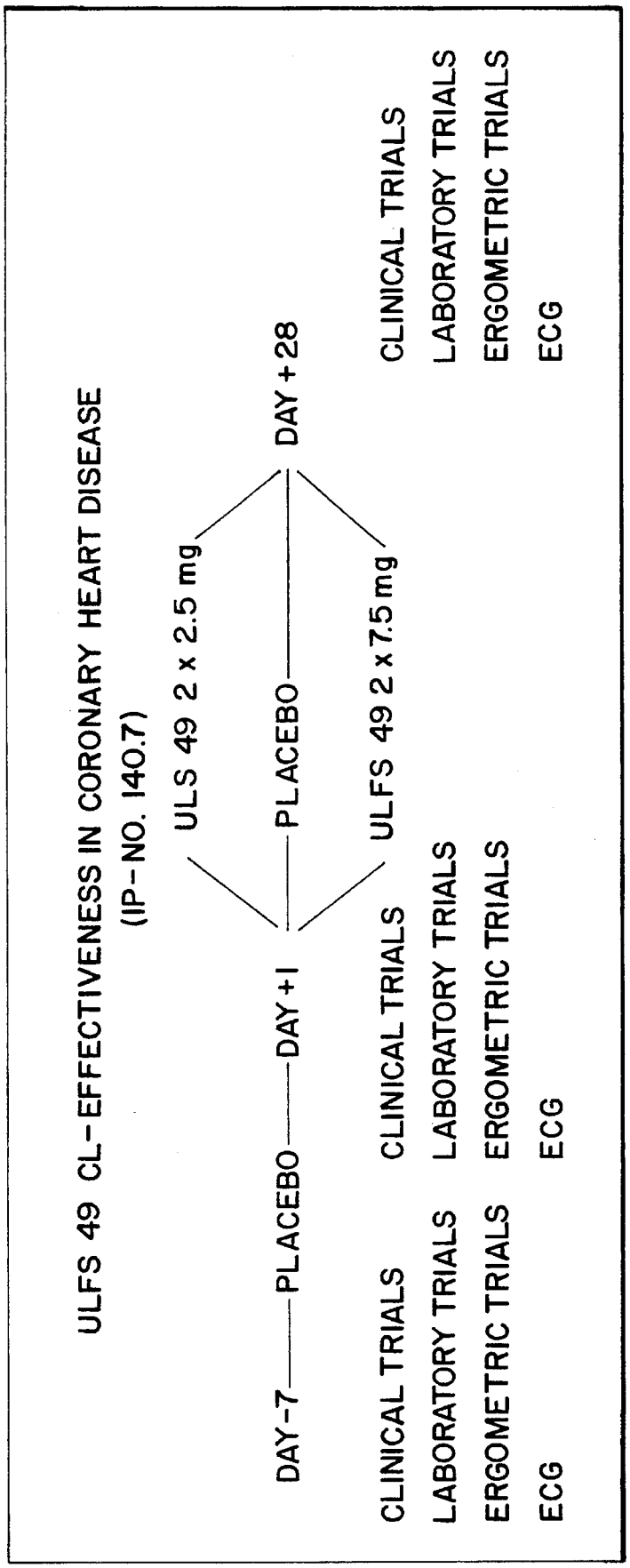
FIG. 1 is a flow diagram showing a course of treatment with the compound ULFS 49CL.

A total of 60 patients were studied in a double blind placebo-controlled clinical trial of the anti-angina effect of UL-FS 49 CL in patients suffering from coronary heart disease. At the start of the trial none of the patients was receiving treatment. In the first week (day −7 to day −1) all 60 patients were given placebo. During the next 4 weeks, the 60 patients were divided into 3 groups of 20 patients. The first group were given more placebo during this period. The second group were given 2×2.5 mg of the active substance and the third group were given 2×7.5 mg of the active substance each day by oral route (see FIG. 1).

On days −7,+1 and +28 the following tests were carried out:

Clinical investigation, laboratory and ECG, heart rate and blood pressure at rest and under stress.

The complete data for 48 patients were available for an intermediate evaluation. As well as a lowering of heart rate and an increase in the duration of stress, a significant reduction in blood pressure was surprisingly found. The data which follow relate to the times 2 hours after administration.

Figure 2:
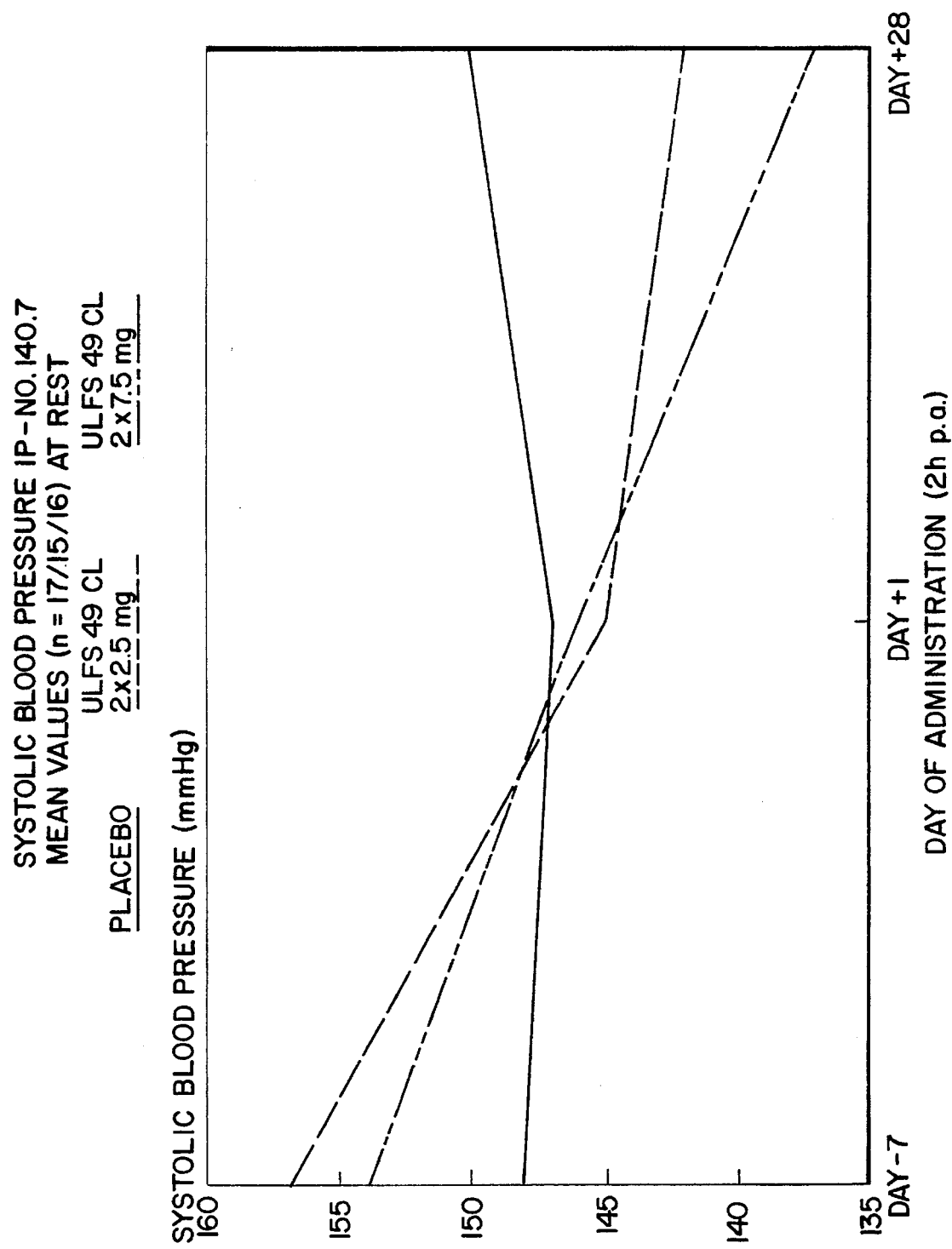
FIG. 2 is a chart of systolic blood pressure values over a period of time during administration of two (2) dosages of ULFS 49CL.
Figure 3:
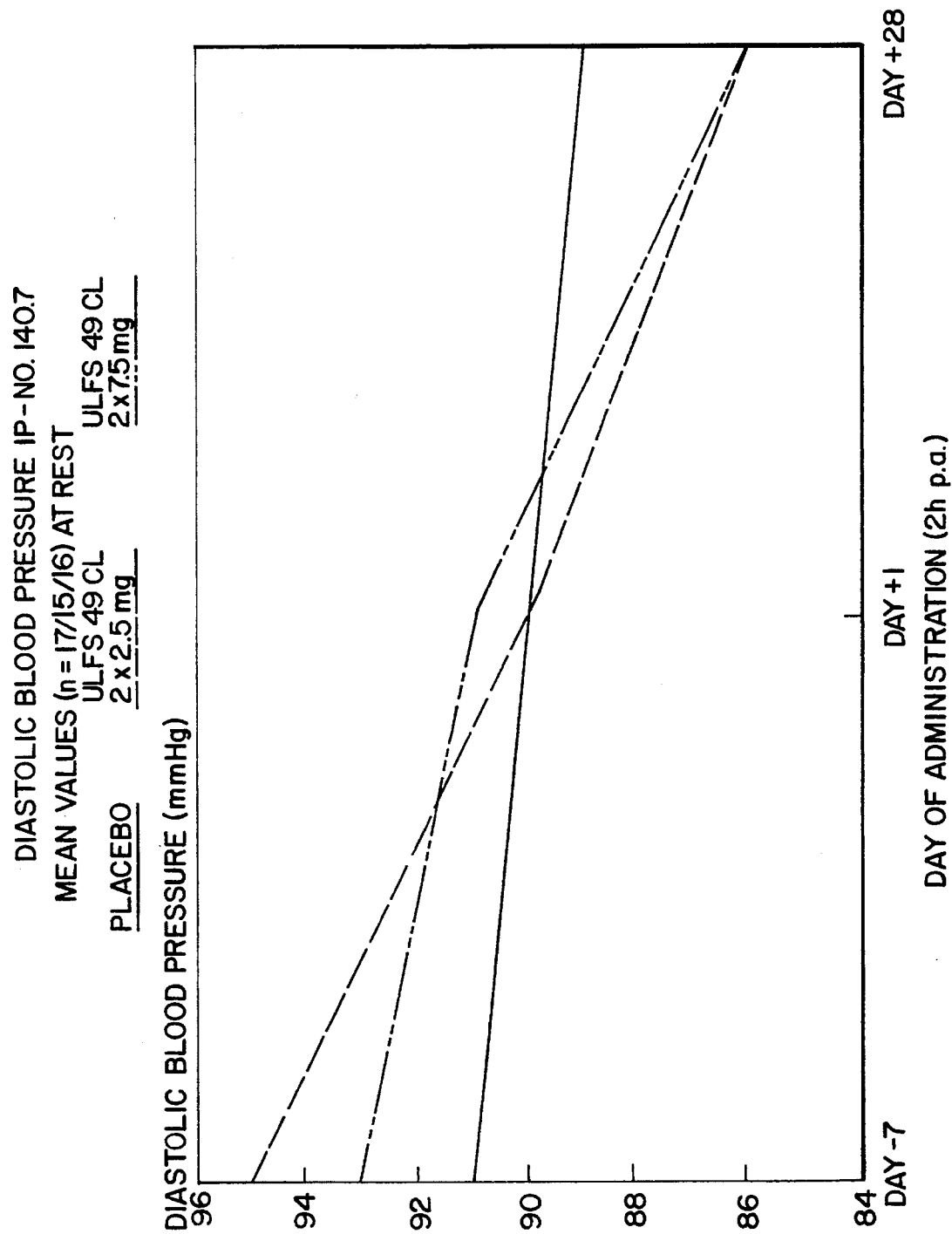
FIG. 3 is a chart of diastolic blood pressure values over a period of time during administration of two (2) dosages of ULFS 49CL.

In the placebo group (n=17) both systolic and diastolic blood pressure were virtually unchanged (Tables 1 and 2) See also FIGS. 2 and 3. In the 2.5 mg group (n=15) systolic blood pressure fell from 157±10 mm Hg (day −7) to 142 ±16 mm Hg (day +28) with p 0.001 (Table 1). See also FIG. 2. In the same period, diastolic blood pressure fell from 95±8 mm Hg to 86±6 mm Hg, again with p 0.001 (Table 2). See also FIG. 3. In the 7.5 mg groups (n=16) systolic blood pressure was lowered from 154±14 mm Hg (day −7) to 137±13 mm Hg (day +28) with p 0.001 (Table 1). See also FIG. 2. In this treatment group, diastolic blood pressure was reduced from 93±8 mm Hg to 86±6 mm Hg with p 0.01 (Table 2). See also FIG. 3.

TABLE 1

Systolic blood pressure

|  | Placebo | 2 × 2.5 mg ULFS 49 | 2 × 7.5 mg ULFS 49 |
| --- | --- | --- | --- |
| Day − 7 | 148 ± 18 | 157 ± 10 | 154 ± 14 |
| Day + 1 | 147 ± 13 | 145 ± 18 | 146 ± 16 |
| Day + 28 | 150 ± 14 | 142 ± 16 | 137 ± 13 |

TABLE 2

Diastolic blood pressure

|  | Placebo | 2 × 2.5 mg ULFS 49 | 2 × 7.5 mg ULFS 49 |
| --- | --- | --- | --- |
| Day − 7 | 91 ± 7 | 95 ± 8 | 93 ± 8 |
| Day + 1 | 90 ± 7 | 90 ± 6 | 91 ± 7 |
| Day + 28 | 89 ± 8 | 86 ± 6 | 86 ± 6 |

Hitherto, the hypotensive effects of UL-FS 49 CL and the acid addition salts thereof have not been described either pharmacologically or clinically/pharmacologically. From the physiological point of view when heart rate is lowered, if anything, an increase in systolic blood pressure with a simultaneous slight lowering diastolic blood pressure can be expected. However, mean arterial pressure would be unchanged.

The present study clearly shows a statistically significant and clinically relevant drop in systolic and diastolic blood pressure.

On the basis of these new findings, the present compounds, especially UL-FS 49 CL, are suitable for the treatment of high blood pressure and/or cardiac insufficiency.

Acute toxicity

The acute toxicity of UL-FS 49 was determined in mice, rats and rabbits by the usual methods. The $LD_{50}$ was calculated from the percentage of animals which died within 14 days after receiving various doses, using the method described by Litchfield and Wilcoxon (J. Pharmacol. exp. Ther., 96, 99 (1949)).

| Type of animal | LD50 mg/kg | |
| --- | --- | --- |
| | oral | parenteral |
| Mouse | 1,350 | i.v. 89 |
| Rat | 479 | — |
| Rabbit | — | i.v. 45 |

EXAMPLE 1

Film coated tablets containing 1.25 mg

A. Tablet core

Composition

| (01) UL-FS 49 CL | 1.25 mg |
| --- | --- |
| (02) Lactose × H₂O | 30.00 mg |
| (03) Corn starch | 16.00 mg |
| (04) Collidone 25 | 2.50 mg |
| (05) Magnesium stearate | 0.25 mg |
|  | 50.00 mg |

Manufacture:

The active substance is thoroughly triturated with 5 mg of (02). The triturated mixture is combined with (03) and the remainder of the (02) and homogeneously moistened with an aqueous solution of (04). The moist substance is passed through a screen with a mesh size of 1.5 mm, dried in a circulating air dryer, screened again (mesh size 1.0 nun) and mixed with (05). From this mixture, tablets with convex sides, 5 mm in diameter and weighing 50 mg are produced in a tablet making machine.

B. Film coating

Composition:

| (01) Hydroxypropylmethylcellulose | 1.5 mg |
| --- | --- |
| (02) Polyethyleneglycol 6000 | 0.3 mg |

Manufacture:

The film components (01) and (02) are dissolved in water and sprayed onto the tablet cores by means of a two-substance nozzle.

Description of a film coated tablet

Apearance: white, round, biconvex

Diameter: approx. 5.1 mg

Weight: approx. 51.8 mg

EXAMPLE 2

Coated tablets containing 1.25 mg

A. Tablet core as in Example 1 A.

B. Tablet coating

Applied by the usual method using a sugar-containing coating suspension in a conventional coating pan.

Description of a coated tablet

Appearance: white, round, biconvex

Diameter: approx. 6 mm

Weight: approx. 70 mg

EXAMPLE 3

Capsule containing 7.5 mg of UL-FS 49 CL

Composition:

1 capsule contains:

| | |
|---|---|
| UL-FS 49 CL | 7.5000 mg |
| Dried corn starch | 85.7500 mg |
| Lactose × 1H$_2$O | 85.7500 mg |
| Magnesium stearate | 1.0000 mg |
| | 180.0000 mg |

Capsule shell:

| | |
|---|---|
| Hard gelatin capsules, No. 3, buff-coloured | 50.0000 mg |
| | 230.0000 mg |

Method of manufacture:

The active substance, corn starch and lactose are mixed together, thoroughly moistened with granulating liquid (ethanol/water 1+1 w/w) and screened.

After drying at 50° C. the granules are screened again and magnesium stearate is then added.

The complete capsule granules are homogeneously mixed and packed into hard gelatin capsules in a suitable capsule-making machine.

EXAMPLE 4

Ampoules containing 5 mg of UL-FS 49 CL

| Composition: | mg/5 ml |
|---|---|
| UL-FS 49 CL | 5.000 mg |
| Citric acid × H$_2$O | 2.000 mg |
| 1N NaOH ad pH 6.0 | about 0.025 ml |
| NaCl | 46.500 mg |
| H$_2$O for injection ad | 5.000 ml |

Method of manufacture:

Citric acid, active substance and sodium chloride are dissolved at ambient temperature in water for injections. The solution is adjusted to pH 6 in 1N NaOH and made up to the required weight with water for injections. After being filtered sterile, the solution is transferred into thin ampoules. The filled ampoules are autoclaved for 20 minutes at 121° C.

EXAMPLE 5

Suppositories containing 10 mg of UL-FS 49 CL

Composition:

| | |
|---|---|
| UL-FS 49 CL | 0.010 g |
| Hard fat | 1.690 g |
| (e.g. Witepsol H 19 and Witepsol W 45) | |
| | 1.700 g |

Method of manufacture:

The hard fat is melted. At 38° C. the ground active substance is homogeneously dispersed in the melt. It is cooled to 35° C. and poured into slightly chilled suppository moulds.

A suppository weighing 1.7 g contains 10 mg of UL-FS 49 CL.

EXAMPLE 6

Drops solution containing 5 mg/1 ml/20 drops of UL-FS 49 CL

Composition:

| | |
|---|---|
| UL-FS 49 CL | 0.50 g |
| Hydroxyethylcellulose | 0.15 g |
| Tartaric acid | 0.10 g |
| Sorbitol solution (70% dry matter) | 30.00 g |
| Glycerol | 10.00 g |
| Benzoic acid | 0.15 g |
| Distilled water ad | 100.00 ml |

Method of manufacture:

The distilled water is heated to 70° C. The hydroxyethylcellulose, benzoic acid and tartaric acid are dissolved therein with stirring. The solution is cooled to ambient temperature and the glycerol and sorbitol solution are added with stirring. At ambient temperature the active substance is added and stirred until completely dissolved. Then the solution is evacuated with stirring to eliminate air.

1 ml, corresponding to 20 drops of the solution, contains 5.0 mg of UL-FS 49 CL.

EXAMPLE 7

Syrup containing 2.5 mg of UL-FS 49 CL/5 ml

Composition:

| | |
|---|---|
| UL-FS 49 CL | 0.05 g |
| Carboxymethylcellulose | 0.10 g |
| Methyl p-hydroxybenzoate | 0.05 g |
| Propyl p-hydroxybenzoate | 0.03 g |
| Sucrose | 10.00 g |
| Glycerol | 5.00 g |
| 70% sorbitol solution | 20.00 g |
| Flavouring | 0.30 g |
| Distilled water ad | 100.00 ml |

Method of manufacture:

Distilled water is heated to 70° C. The methyl p-hydroxybenzoate and propyl p-hydroxybenzoate and the glycerol and carboxymethylcellulose are dissolved therein with stirring. The mixture is cooled to ambient temperature and the active substances is added and dissolved therein with stirring. After the sucrose, sorbitol solution and flavouring have been added and dissolved therein, the syrup is evacuated with stirring to eliminate air.

5 ml of syrup contain 2.5 mg of UL-FS 49 CL.

What is claimed is:

1. A method of treating cardiac insufficiency in a warm-blooded animal which comprises administering to said animal a therapeutically effective amount of a compound of formula

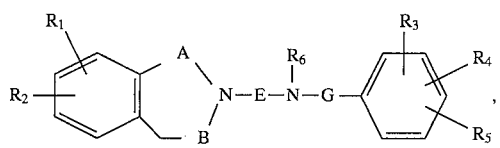

wherein

A is a $-CH_2-CH_2-$, $-CH=CH-$,

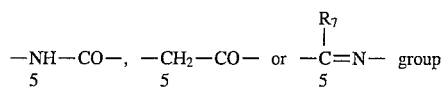

$-NH-CO-$, $-CH_2-CO-$ or $-C=N-$ group wherein $R_7$ is an alkyl group having 1 to 3 carbon atoms, and B is a methylene or carbonyl group or A is a $-CO-CO-$ group and B is a methylene group, E is an ethylene, n-propylene or n-butylene group optionally substituted by an alkyl group with 1 to 3 carbon atoms, an n-propylene group substituted by a hydroxy group in the 2 position or an n-butylene group substituted by a hydroxy group in the 2 or 3 position, G represent a methylene or ethylene group optionally substituted by an alkyl group with 1 to 3 carbon atoms, $R_1$ and $R_2$, which may be identical or different, are hydroxy groups, alkyl, alkoxy or phenylalkoxy groups in which the alkyl moiety may contain from 1 to 3 carbon atoms, or one of the groups $R_1$ or $R_2$ may also represent a hydrogen atom or $R_1$ together with $R_2$ is an alkylenedioxy group with 1 or 2 carbon atoms, $R_3$ and $R_4$, which may be identical or different, are hydrogen or halogen atoms, hydroxy groups, alkyl or alkoxy groups each having 1 to 4 carbon atoms, trifluoromethyl or cyano groups or one of the groups $R_3$ or $R_4$ is a nitro group or $R_3$ together with $R_4$ is an alkylenedioxy group with 1 or 2 carbon atoms, $R_5$ is a hydrogen atom, an alkyl, hydroxy, alkoxy, amino, alkylamino, dialkylamino, alkanoylamino, alkoxycarbonylamino or bis(alkoxycarbonyl)amino group wherein the alkyl part may contain from 1 to 3 carbon atoms, or a methylamino or ethylamino group substituted by a trifluoromethyl group, and $R_6$ is a hydrogen atom, an alkyl, phenylalkyl, alkanoyl or alkoxycarbonyl group in which the alkyl moiety may contain from 1 to 3 carbon atoms or an alkylene group with 3 to 5 carbon atoms.

and the physiologically acceptable acid addition salts thereof with inorganic or organic acids.

2. The method as recited in claim 1, characterized in that 1,3,4,5-tetrahydro-7,8-dimethoxy-3-[3-[[2-(3,4-dimethoxyphenyl)ethyl] methyl]amino]propyl]-2H-3-benzazepin-2-one or one of the physiologically acceptable acid addition salts thereof is administered.

3. The method as recited in claim 2, characterized in that the hydrochloride is administered as the acid addition salt.

* * * * *